United States Patent
Silveira Nogueira Reis et al.

(10) Patent No.: US 12,011,256 B2
(45) Date of Patent: Jun. 18, 2024

(54) DEVICE AND METHOD FOR DETERMINING GESTATIONAL AGE

(71) Applicants: UNIVERSIDADE FEDERAL DE MINAS GERAIS—UFMG, Belo Horizonte (BR); FUNDAÇÃO DE AMPARO À PESQUISA DO ESTADO DE MINAS GERAIS—FAPEMIG, Belo Horizonte (BR)

(72) Inventors: Zilma Silveira Nogueira Reis, Belo Horizonte (BR); Rodney Nascimento Guimarães, São Félix (BR)

(73) Assignees: UNIVERSIDADE FEDERAL DE MINAS GERAIS—UFMG (BR); FUNDAÇÃO DE AMPARO À PESQUISA DO ESTADO DE MINAS GERAIS—FAPEMIG (BR)

( * ) Notice: Subject to any disclaimer, the term of this patent is extended or adjusted under 35 U.S.C. 154(b) by 1207 days.

(21) Appl. No.: 16/346,833

(22) PCT Filed: Nov. 1, 2017

(86) PCT No.: PCT/IB2017/056786
§ 371 (c)(1),
(2) Date: May 1, 2019

(87) PCT Pub. No.: WO2018/083602
PCT Pub. Date: May 11, 2018

(65) Prior Publication Data
US 2020/0178847 A1    Jun. 11, 2020

(30) Foreign Application Priority Data

Nov. 1, 2016   (BR) ...................... 10 2016 025602 0
Oct. 31, 2017  (BR) ...................... 10 2017 023568 8

(51) Int. Cl.
*A61B 5/103* (2006.01)
*A61B 5/00* (2006.01)

(52) U.S. Cl.
CPC .......... *A61B 5/1032* (2013.01); *A61B 5/0075* (2013.01); *A61B 5/4362* (2013.01); *A61B 2503/02* (2013.01); *A61B 2503/045* (2013.01)

(58) Field of Classification Search
CPC ... A61B 5/1032; A61B 5/0075; A61B 5/4362; A61B 2503/02; A61B 2503/045
See application file for complete search history.

(56) References Cited

U.S. PATENT DOCUMENTS

| 5,353,790 | A  | 10/1994 | Jacques et al. | 128/633 |
| 6,882,873 | B2 | 4/2005  | Samuels et al. | 600/315 |

(Continued)

FOREIGN PATENT DOCUMENTS

| BR | 8100051      | 9/2002  | ............ B42D 15/00 |
| CA | 2697316 A1 * | 9/2010  | ........... A61B 5/0059 |

(Continued)

OTHER PUBLICATIONS

Computer Program. Registration No. 5120160005-1, Registration Date: May 6, 2016, title: "Determinação Automática Da Espessura De Epiderme Em Imagens De Ultrassom" (Automatic Determanation of Epidermis Thickness in Ultrasound Images), Institutiona of Registration: INPI—National Institute of Industrial Property, with machine translation (2 pgs).

(Continued)

*Primary Examiner* — Ashley K Buran
*Assistant Examiner* — Helene Bor
(74) *Attorney, Agent, or Firm* — HAYES SOLOWAY P.C.

(57) ABSTRACT

Described is a device for determining gestational age and methods for determining gestational age at birth by measuring parameters associated with photobiological properties of (Continued)

the skin such as reflectance or reflectivity by measuring diffused or scattered portions of the light beam incident on the skin, as well as the erythema index, along with clinical parameters of the newborn such as gender, the use of phototherapy, birth weight and time spent in incubator. The ability to obtain a realistic estimate of the age of the conceptus quickly, non-invasively and at low cost makes it possible to provide care suited to the needs of the newborn, to assess the chances of survival and to affect the short- and long-term prognosis of the newborn. The correct determination of gestational age at birth also influences clinical follow-up protocols in infancy and vital statistics.

13 Claims, 4 Drawing Sheets

(56) References Cited

U.S. PATENT DOCUMENTS

| | | | |
|---|---|---|---|
| 6,927,843 B2 | 8/2005 | Dick | 356/39 |
| 10,729,383 B2 * | 8/2020 | Shin | A61B 5/7405 |
| 2010/0168586 A1 * | 7/2010 | Hillman | A61B 5/0064 |
| | | | 348/E13.001 |
| 2015/0168419 A1 * | 6/2015 | Kenny | G01N 33/92 |
| | | | 506/12 |

FOREIGN PATENT DOCUMENTS

| | | | | |
|---|---|---|---|---|
| CN | 101793824 A | * | 8/2010 | A61B 5/0059 |
| CN | 104376191 | | 2/2015 | G06F 19/00 |
| EP | 1914553 A1 | * | 4/2008 | G01N 33/6893 |
| JP | H05161609 A | * | 6/1993 | A61B 5/0059 |
| JP | 2002148778 A | * | 5/2002 | |
| PH | 12010000074 B1 | * | 9/2010 | |

OTHER PUBLICATIONS

Ersch et al., Assessing gestational age from the histology of fetal skin: an autopsy study of 379 fetuses. Obstetrics & Gynecology, 1999; 94 (S, Part 1): 753-7 (5 pgs).

International Search Report and Written Opinion (w/translation) issued in application No. PCT/IB2017/056786, dated Feb. 26, 2018 (20 pgs).

Kenner et al., Comprehensive Neonatal Care: An Interdisciplinary Approach, Fourth Edition, 2007, internet link: https://books.google.com.br/books?hl=en&lr=&id=7eV2l1x33owC&oi=fnd&pg=PA1&dq=Comprehensive+Neonatal+Care:+An+Interdisciplinary+Approach+by+Carole+Kenner+and+Judy&ots=46taHtMXA0&sig=oLLKVp5yKnIWBDECxADAeUyty5g#v=onepage&q=Comprehensive%20Neonatal%20Care%3A%20An%20Interdisciplinary%20Approach%20by%20Carole%20Kenner%20and%20Judy&f=false.

Lister et al., Optical properties of human skin. Journal of biomedical optics, 2012; 17(9): 0909011-09090115 (16 pgs).

Lynn et al., Gestational Age Correlates With Skin Reflectance in Newborn Infants of 24-42 Weeks Gestation, 1993, abstract only (1 pg).

Sherwood et al., Fetal age: methods of estimation and effects of pathology, American Journal of Physical Anthropology, 2000, 13 (3): 305-15) (11 pgs).

Silva et al. editors. An image processing tool to support gestational age determination. 19th IEEE Symposium on Computer-Based Medical Systems (CBMS'06), 2006: IEEE (6 pgs).

* cited by examiner

DEVICE AND METHOD FOR DETERMINING GESTATIONAL AGE

The present application patent describes a device for determining gestational age; methods for determining the gestational age at birth by measuring parameters associated with the photobiological properties of the skin and clinical parameters of newborns. The technology makes it possible to determine gestational age at birth using photobiological properties of the skin such as the reflectance or reflectivity by measuring the diffused or scattered portions of the light beam incident on the skin, as well as the erythema index, along with clinical parameters of the newborn such as gender, the use of phototherapy, birth weight and time spent in incubator. The technology provides many advantages, since the ability to obtain a realistic estimate of the age of the conceptus quickly, non-invasively and at low cost makes it possible to provide care suited to the needs of the newborn, to assess the chances of survival and to affect the short- and long-term prognosis of the newborn. In terms of population, it facilitates recognition of prematurity, which is relevant to public health policy worldwide. The correct determination of gestational age at birth also influences clinical follow-up protocols in infancy and vital statistics.

In the context of forensic anthropology and archeology, the identification of the age of a conceptus from limited quantities of human material has singular importance. Also, in these conditions, it is necessary to associate the number of potential indicators of gestational chronology with those already existing (Sherwood R. J., Meindl R., Robinson H., May F. Fetal age: methods of estimation and effects of pathology, American Journal of Physical Anthropology, 2000, 13 (3): 305-15).

There are some technologies intended to determine the gestational age of newborns that, although they have the same purpose of the proposed invention, present distinct characteristics in relation to the presented technology. The following documents can be highlighted:

U.S. patent US2015168419 of Nov. 16, 2010 titled PREDICTION OF A SMALL-FOR-GESTATIONAL AGE (SGA) INFANT describes a method capable of predicting the gestational age of a patient from the analysis of a set of metabolites that are indicated as biomarkers and their respective blood abundances, which differs from the proposed technology that uses photobiological skin properties and clinical parameters of the newborn to determine the gestational age.

Patent CN104376191 of Aug. 16, 2013 titled GESTATIONAL AGE PREDICTION METHOD AND DEVICE describes a method and device capable of predicting the gestational age of a patient from the analysis of a set of anthropometric measurements performed on the fetus, which differs from the proposed technology that uses photobiological properties of the skin and clinical parameters of the newborn to determine the gestational age.

Utility model MU8100051-0 of Jan. 8, 2001 titled TABELA PAPA IDADE GESTACIONAL describes a method that relates information, from prenatal exams to gestational age in a table and enables an estimate of gestational age, which differs from the proposed technology that uses photobiological skin properties and clinical parameters of the newborn to determine the gestational age.

U.S. Pat. No. 5,353,790 of Jan. 17, 1992 titled METHOD AND APPARATUS FOR OPTICAL MEASUREMENT OF BILIRUBIN IN TISSUE and the article titled GESTATIONAL AGE CORRELATES WITH SKIN REFLECTANCE IN NEWBORN INFANTS OF 24-42 WEEKS GESTATION by Lynn. C. J. Saidi. I. S., Oelberg D. G. and Jacques SL, 1993, describes studies indicating the existence of a correlation between gestational age and skin reflectance in newborns, which are independent of the pigmentation or gender of the newborn. The article discusses the relation between the maturation of the skin and the increase of the collagen fibers together with the relation of these characteristics with the gestational age, also correlates the scattering coefficient with the interaction thereof with the collagen fibers present in the skin. The skin scattering coefficient was measured at wavelengths in the range of 380 to 820 nm. This document differs from the proposed technology because it does not use photobiological properties of the skin and clinical parameters of the newborn to determine gestational age.

The selected studies that will be shown next present a part of the knowledge that composed the state of the art until the moment immediately before the development of the proposed technology and represented a starting point for the development of the presented methods and device.

The skin development in layers is continuous and directly related to gestational age. It is believed that skin thickness is one of the evolutionary markers of this development that, in intrauterine life, is continuous, and there are patterns related to fetal age that are recognizable by microscopy, as they reflect the gradual histogenesis of the dermis, epidermis and skin appendages. Such microscopic imaging standards, assessed by specialists, are capable of predicting gestational age with 97% agreement with the gold standard, the early obstetric ultrasound, between 15 and 30 weeks of pregnancy (Ersch J., Stallmach T., Assessing gestational age from the histology of fetal skin: an autopsy study of 379 fetuses. Obstetrics & Gynecology, 1999; 94 (5, Part 1): 753-7), (Computer Program. Registration Number: 5120160005-1, Registration Date: May 6, 2016, title: "DETERMINAÇÃO AUTOMÁTICA DA ESPESSURA DE EPIDERME EM IMAGENS DE ULTRASSOM" (AUTOMATIC DETERMINATION OF EPIDERMIS THICKNESS IN ULTRASOUND IMAGES), Institution of Registration: INPI—National Institute of Industrial. Property).

The book Comprehensive Neonatal Care: An Interdisciplinary Approach by Carole Kenner and Judy Wright Lott, Fourth Edition, 2007, describes the direct relation between gestational age and the presence of keratin in the skin.

Human skin absorbs and scatters photons emitted by optical devices. Scattering and absorption are properties that represent the nature of this interaction. The absorption of light basically depends on the concentrations of its proteins such as melanin, collagen and keratins and the scattering caused by hemoglobin that, however, is spatially distributed at varying depths (Lister T., Wright P. A., Chappell P. H., Optical properties of human skin. Journal of biomedical optics, 2012; 17(9): 0909011-09090115).

Optical methods are effective for the evaluation of superficial layers of the skin, epidermis and dermis, since multiple deep layer scatterings prevent good penetration of the light signal. Estimated skin thickness, separated into its dermal and epidermal layers, was described from the near-infrared diffuse reflection spectroscopy, 0.79 and 25.80 microns, 0.72 and 21.87 microns and 0.77 microns and 8.16, respectively, for total thickness, epidermis and dermis.

FootScanAge is a technology that uses an approach that allows the estimation of gestational age from the analysis of the characteristics of the image of the newborn plantar surface. The method consists of automated image processing, followed by data mining and identification of patterns characteristic of the chronological progression of Pregnancy (Silva L., Bellon O. R. P., Lames RdP, Meira J. A., Cat MN, editors. An image processing tool to support gestational age determination. 19th IEEE Symposium on Computer-Based Medical Systems (CBMS'06), 2006: IEEE).

The state of the art presented points to a number of studies and technologies for determining gestational age, but none of them uses photobiological properties of the skin and clinical parameters of the newborn. Some presented studies and technologies demonstrate relations between newborn skin optical properties, such as the skin scattering coefficient, which depends on the adoption of a previous model of the skin, which relate to gestational age, but do not describe a method and/or device to determine the gestational age at birth in an objective and sufficient way as proposed by the present technology.

The present invention provides a device and method for determining gestational age by using photobiological properties of the skin such as reflectance or reflectivity by measuring the diffused or scattered portions of the light beam incident on the skin, in addition to the index of erythema together with clinical parameters of the newborn such as the gender, the use of phototherapy, birth weight and incubator stay; nor do they present a device capable of emitting light on the skin and measuring the portion of light that has been scattered both forwards and backwards after the interaction with the chromophores present in the layers forming the skin.

DETAILED DESCRIPTION OF THE TECHNOLOGY

The present patent application describes a device for determining gestational age and methods for determining gestational age at birth. The technology is based on parameter measurements associated with skin photobiological properties such as reflectance or reflectivity by measuring the diffused or scattered portions of the light beam incident on the skin and clinical parameters of newborns such as gender, the use of phototherapy, birth weight and incubator stay. The proposed device is capable of emitting light onto the skin at wavelengths comprised in the following ranges: 395-405, 625-635, 530-540 nm. In addition, it is capable of measuring the portion of light that has been scattered, both forwards and backwards, after the interaction with the chromophores present in the layers forming the skin.

Figure 1:
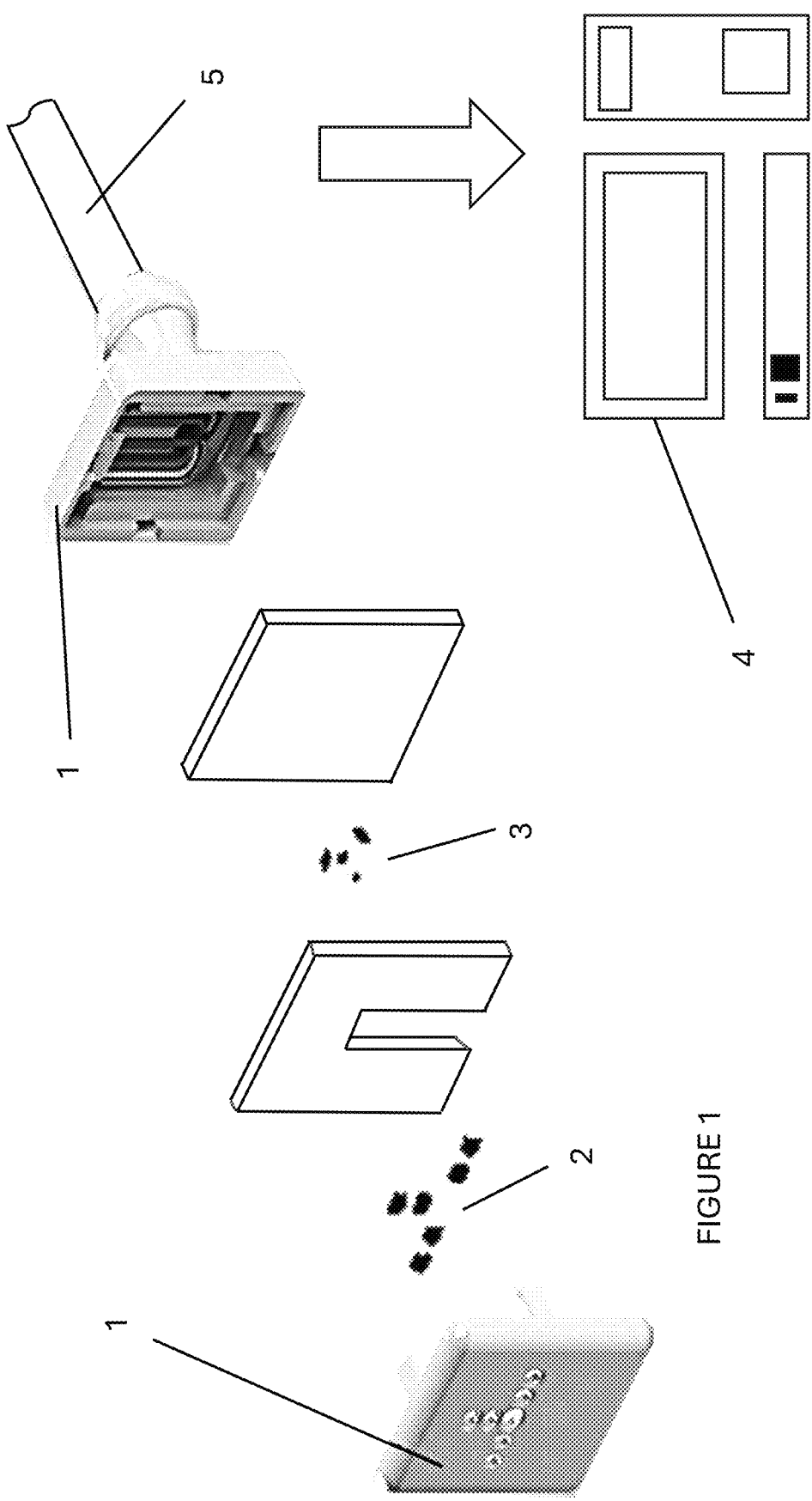
FIG. 1 shows a possible, non-limiting embodiment of the device and its constituent parts: holder (1); light emitting element (2); sensor element (3) capturing a considerable part of the light signal coming from (2) and turning it into electrical energy or a frequency signal; at least one computer with a display unit (4); signal transmission guide elements (5) carrying the signals between (2), (3), and (4).

The device comprises a holder (1) enclosing at least one light emitting element (2); at least one sensor element (3) capturing a considerable part of the light signal coming from (2), which was reflected by the skin or its components, or part of the light signal emitted by the skin components as a consequence of the interaction thereof with the light emitted by (2), and turns this light signal into electrical energy or a frequency in order to make possible the quantification of light intensity that was diffusedly reflected or scattered by the biological components of the skin and turns this light signal into electrical energy or frequency; at least one computer (4) with an architecture allowing the provision of the input, output and conversion of analogical and digital signals and also allowing the input, the output, the display, the storage, and the processing of data, in addition to making calculations; at least a pair of signal transmission guide elements (5) carrying the signals between (2), (3), and (4), wherein the device is represented in a non-limiting way in FIG. 1.

The light emitter element (2) in its preferred configuration emits light at the wavelengths comprised in the following ranges 395-405, 625-635, 530-540 nm. The range 395-405 nm corresponds to the blue color that is suitable for determining the melanin and keratin concentration, and the ranges 625-635 nm and 530-540 nm correspond to the red and green colors, respectively, which are suitable for determining the concentration of collagen and erythema index (hemoglobin concentration) among other chromophores. The determination of the erythema index is performed by means of expression (1), where $R_1$ is the reflectance measured from the red light beam (625-635 nm), which distance between the light emitter element (2) and the sensor (3) measuring the scattered portion of this light beam is 3 mm and $R_2$ is the reflectance measured from the green light beam (530-540 nm) whose distance between the light emitter element (2) and the sensor (3) measuring the scattered portion of this light beam is 3 mm.

$$Log_{10}(R_1-R_2) \qquad (1)$$

The light emitter (2), in its preferred configuration, is a light emitting diode (LED) and the sensor (3) is preferably a photodiode.

The device may preferentially be configured so that there is redundancy of the light emitter element (2) on the same wavelength and the redundant elements (2) are spaced apart from the sensor element (3) at different distances, in order to allow the cancellation of light interferences.

The signal transmission guide elements (5) preferentially are conductor wires, transmission fibers of optical signals used independently or in combination.

The proposed methods for determining gestational age at birth are based on photobiological properties of the skin such as reflectance or reflectivity by measuring the diffused or scattered portions of the light beam incident on the skin, in addition to the erythema index along with clinical parameters of the newborn such as gender, the use of phototherapy, birth weight and incubator stay.

Three methods were obtained to determine gestational age at birth; 1) a method for determining gestational age at birth from photobiological skin properties: red light scattering; 2) a method for determining gestational age at birth from photobiological skin properties: red and blue light scattering; 3) a method for determining gestational age at birth from photobiological skin properties: erythema index, red and blue color light scattering, and clinical parameters of newborns. There follow the methods:

Method 1—

A method for determining gestational age at birth from skin photobiological properties: red light scattering, which comprises the following steps:
 a) falling a light beam with 625-635 nm of wavelength on the skin of the newborn foot;
 b) measuring the scattered light intensity from the light beam with 625-635 nm of wavelength applied to the skin of the newborn foot, according to step a), by means of a sensor positioned at a distance of 2-4 mm from the source that generated the light beam with 625-635 nm of wavelength;
 c) measuring the backscattered/scattered light intensity from the light beam with 625-635 nm of wavelength applied to the skin of the newborn foot according to step a) by means of a sensor positioned at a distance of 4-7 mm from the source which generated the light beam with 625-635 nm of wavelength;
 d) calculating the ratio (x) between the light intensity measured in step c) and the light intensity measured, in step b)
 e) calculating the gestational age (GA), in weeks, by replacing the value of the ratio (x) obtained in step c) with the variable (x) of expression (2): GA=44.75−(48.93/x).

Method 2—

A method for determining gestational age at birth from skin photobiological properties: red and blue light scattering, which comprises the following steps:
 a) falling a light beam with 625-635 nm of wavelength on the skin of the newborn foot;
 b) falling a light beam with 440-485 nm of wavelength on the skin of the newborn foot;
 c) falling a light beam with 530-540 nm of wavelength on the skin of the newborn foot;
 d) measuring the backscattered scattered light intensity from the light beam with 625-635 nm of wavelength applied to the skin of the newborn foot according to step a) by means of a sensor positioned at a distance of 2-4 mm from the source which generated the light beam with 625-635 nm of wavelength;
 e) measuring the backscattered/scattered light intensity from the light beam with 625-635 nm of wavelength applied to the skin of the newborn foot according to step a) by means of a sensor positioned at a distance of 4-7 mm from the source which generated the light beam with, 625-635 nm of wavelength;
 f) measuring the backscattered/scattered light intensity, from the light beam with 440-485 nm of wavelength applied to the skin of the newborn foot according to step b) by means of a sensor positioned at a distance of 2-4 mm from the source which generated the light beam with 440-485 nm of wavelength;
 g) measuring the backscattered; scattered light intensity from the light beam with 530-540 nm of wavelength applied to the skin of the newborn foot according to step c) by means of a sensor positioned at a distance of 2-4 mm from the source which generated the light beam with 530-540 nm of wavelength;
 h) calculating the ratio ($x_1$) between the light intensity measured in step e) and the light intensity measured in step d);
 i) calculating the logarithm for the base 10 ($x_3$) of the subtraction between the light intensity measured in step d) and the light intensity measured in step g) representing the erythema index;
 j) calculating the gestational age (GA), in weeks, using expression (3):

$$GA=1.995x_1+(1.156\times10^{-5})x_2+9.357x_3-31.767 \qquad (3),$$

by replacing the value of the ratio ($x_1$) obtained in step h) with the variable ($x_1$) of expression (3), the value of the reflectance obtained in step f) with the variable ($x_2$) of expression (3); the value of the logarithm obtained in step i) with the variable ($x_3$) of expression (3).

Method 3—

A method for determining gestational age at birth from skin photobiological properties: red and blue light scattering and clinical parameters of newborns, which comprises the following steps:
 a) falling a light beam with 625-635 nm of wavelength on the skin of the newborn foot;
 b) falling a light beam with 440-485 nm of wavelength on the skin of the newborn foot;
 c) falling a light beam with 530-540 nm of wavelength on the skin of the newborn foot;
 d) measuring the backscattered/scattered light intensity from the light beam with 625-635 nm of wavelength applied to the skin of the newborn foot according to step a) by means of a sensor positioned at a distance of 2-4 mm from the source which generated the light beam with 625-635 nm of wavelength;
 e) measuring the backscattered/scattered light intensity from the light beam with 625-635 nm of wavelength applied to the skin of the newborn foot according to step a) by means of a sensor positioned at a distance of 4-7 mm from the source which generated the light beam with 625-635 nm of wavelength;
f) measuring the backscattered/scattered light intensity from the light beam with 440-485 nm of wavelength applied to the skin of the newborn foot according to step b) by means of a sensor positioned at a distance of 2-4 mm from the source which generated the light beam with 440-485 nm of wavelength;
g) measuring the backscattered/scattered light intensity from the light beam with 530-540 nm of wavelength applied to the skin of the newborn foot according to step c) by means of a sensor positioned at a distance of 2-4 mm from the source which generated the light beam with 530-540 nm of wavelength;
h) calculating the ratio (x) between the light intensity measured in step e) and the light intensity measured in step d);
i) calculating the logarithm for the base 10 ($x_3$) of the subtraction between the light intensity measured in step d) and the light intensity measured in step g);
j) obtaining information on the birth weight of the newborn (in grams);
k) obtaining information on the gender of the newborn (male/female=1/0);
l) obtaining information on whether the newborn is in the incubator at the time of measurement with the device (yes/no=1/0);
m) obtaining information on whether the newborn is using phototherapy at the time of measurement with the device (yes/no=1/0);
n) calculating the gestational age (GA), in weeks, using expression (4):

$$GA=12.143-20.995x_1+(3.544\times 10^{-6})x_2+3.746x_3+0.002x_4-0.179x_5-0.855x_6-0.403x_7 \quad (4),$$

by replacing the value of the ratio ($x_1$) obtained in step h) with the variable ($x_1$) of expression (4), the value of the reflectance obtained in step f) with the variable ($x_2$) of expression (4); the value of the logarithm obtained in step i) with the variable (x) of expression (4); the value of the newborn weight obtained in step j) with the variable ($x_4$) of expression (4); the value (0 or 1) of the newborn gender obtained in step k) with the variable ($x_5$) of expression (4); the value (0 or 1) of the information on whether the newborn is in the incubator obtained in step l) with the variable ($x_6$) of expression (4); the value (0 or 1) of the information on whether the newborn is using phototherapy obtained in step m) with the variable ($x_7$) of expression (4)

The present invention can be better understood by means of non-limiting examples of the technology, as follows.

Example 1. Study of the Measurement of Skin Reflectivity at Center Wavelengths of 470, 535, 630 nm Carried Out with a Device Prototype The correlation between light scattering and gestational age at birth of newborns was demonstrated by the inventors by means of a study that used light scattering measurements at several wavelengths of a set of 115 (n=115) newborns. These measurements were obtained at several parts of the body (foot, forearm, umbilicus and hand); the measurements were performed in two moments: in the first 24 hours of life (day 1) and 24 hours after the first evaluation (day 2). The gestational age was estimated from the obstetric ultrasound had up to 13 weeks of pregnancy. The analysis of correlation between light scattering and gestational age at birth with data gathered by gestational age and measurement place are presented in Table 1. Parameters r and p are the correlation coefficient and the significance level, respectively.

TABLE 1

Values of scattering (diffuse reflectance × 106) and measurement place in first and second days after birth, obtained with the prototype

| Measurement characteristics: | Forearm Average (standard deviation) | | | Foot sole Average (standard deviation) | | | Difference in reflectance between forearm and foot sole | |
|---|---|---|---|---|---|---|---|---|
| Waveleagth (nm)/ Distance between LED and Sensor (nm) | Day 1 (n = 94) | Day 2 (n = 85) | Difference between Days 1 and 2 P-value* | Day 1 (n = 94) | Day 2 (n = 87) | Difference between Days 1 and 2 P-value* | Day 1 (n = 190) P-value* | Day 2 (n = 172) P-value* |
| 630/3.3 | 0.438 (0.166) | 0.443 (0.166) | 0.830 | 0.504 (0.111) | 0.499 (0.001) | 0.730 | 0.001[#] | 0.007[#] |
| 630/6.5 | 0.081 (0.033) | 0.077 (0.029) | 0.372 | 0.105 (0.031) | 0.090 (0.022) | <0.001[#] | <0.001[#] | 0.001[#] |
| 575/6.5 | 0.002 (0.008) | 0.001 (0.001) | 0.203 | 0.002 (0.005) | 0.002 (0.001) | 0.175 | 0.996 | 0.094 |
| 575/3.3 | 0.004 (0.007) | 0.003 (0.001) | 0.110 | 0.005 (0.005) | 0.004 (0.002) | 0.022 | 0.476 | 0.017[#] |
| 470/6.5 | 0.029 (0.042) | 0.026 (0.041) | 0.669 | 0.028 (0.009) | 0.035 (0.046) | 0.156 | 0.733 | 0.208 |
| 470/3.3 | 0.214 (0.174) | 0.186 (0.065) | 0.175 | 0.0260 (0.089) | 0.023 (0.082) | 0.030[#] | 0.024[#] | <0.001[#] |

*P-value: Student t-Test;
[#]correlation with statistically significant values

The results presented in Table 1 demonstrate that there is a significantly higher scattering of light for wavelengths in the red part of the spectrum (630 nm) and for smaller distances between LEDs and SENSOR (3.3 mm), it is possible to conclude that there is not a great difference of scattering in the first 48 hours of life of the newborns.

The device developed uses LEDs and photodiodes to measure the amount of reflected light (backscattering) by the biological components of the skin, specifically the direct measurement of the reflectivity of the skin. Accordingly, at least two properties are indirectly determined; the erythema index using the green (535 nm) and red (630 nm) lights and the reflectivity of the skin in red (630 nm) and blue (470 nm) lights. The following assumptions guided the construction of the device;

In the design for the construction of the device, the multilayer model of the skin was adopted, wherein these sublayers are; stratum corneum, epidermis, dermis, hypodermis, etc. In this way, the light from the LEDs penetrates the skin being scattered (diffuse reflection) by the constituents of these layers and at the boundary between them.

There is a relation between the depth of optical penetration of light into the skin, as a function of wavelength, so that the light reaches only the upper layers of the skin, such as the stratum corneum and the epidermis, there must be used light with small wavelengths such as blue and ultraviolet (UV).

The existence of a relation, regarding the distance between the LEDs and the photodiode and the depth of light penetration into the skin, that is, the smaller the distance between LEDs and the photodiode, the more superficially the light will penetrate the skin, reaching only the upper layers, the stratum corneum and the epidermis.

Based on these assumptions, a device was constructed to measure the concentration of keratin and consequently gestational age.

The constructed device consists of six Light Emitting Diode (LED) light sources, a photodiode, a printed circuit board (PCB) and an optical barrier surrounding the photodiode. The six LEDs have 3 distinct center wavelengths, 470, 535, 630 nm, which correspond to the colors blue, green and red in the visible region of the electromagnetic spectrum. The same colored LED light sources are side by side at different distances from the photodiode, 3.3 and 6.5 mm respectively. The photodiode chosen was the TEL237LF due to its high sensitivity and to directly convert light into frequency.

The sensor module required an encapsulation to make it more robust, amenable to cleaning/disinfection and easily operable. The a special ergometry cover was designed for the sensor module, which would avoid strong operator pressure against the newborn skin, which would cause a variation in the reflectivity measurements caused by possible changes in the optical path of the light rays emitted by the LED and reflected in the layers of the skin.

The constructed device has a control system that takes into account the need for the LEDs to require a regulated source to keep the current constant in each of them; the circuit allows that, although the currents are constant, they are also different for each color. It is also possible to control the sequence in which each one will be connected. The controller circuit reads a configuration file containing the initial settings of the device, such as: the time interval between the push of the on button and the positioning of the sensor module in the newborn and a hexadecimal value that will control the current supplied to the LEDs.

The controller module has a micro USD input for an external power source and two outputs, one with a micro USE port and another for connecting the sensor module.

The fact that the power source is connected externally, rather than being attached to the control module, is a safety measure. Separating the control module from the power source (external battery) makes the device even safer for later approval at ANVISA (National Agency of Sanitary Surveillance).

Figure 2:
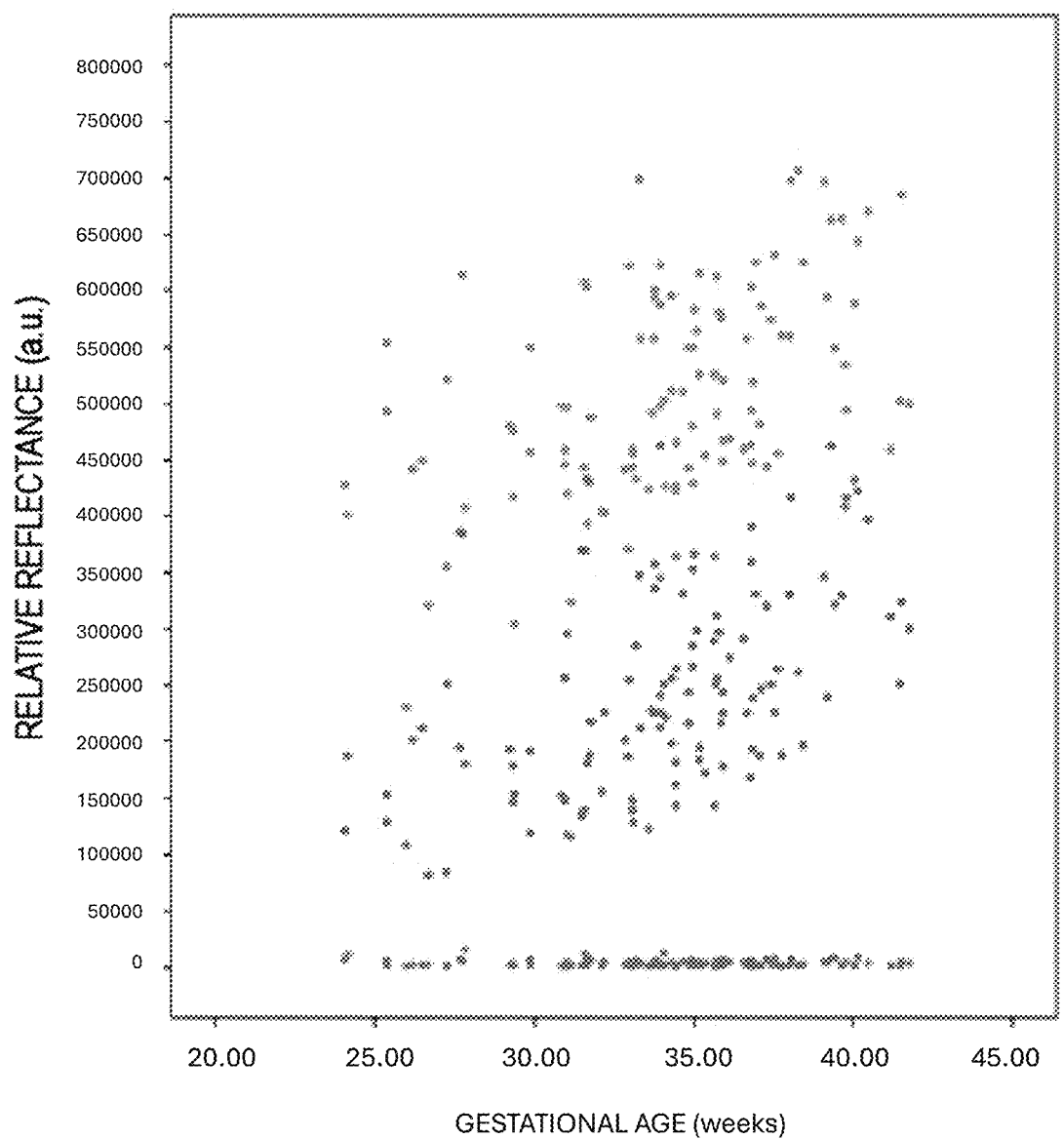
FIG. 2 shows a graph obtained as a result of using the non-limiting configuration of the proposed device according to example 1 of this patent document. The graph represents the relative diffuse reflectivity of the skin (ordinate axis) illuminated by the LEDs at the center wavelengths of 440-465 nm, 530-540 nm, 625-635 nm (respectively, blue, green and red colors) as a function of gestational age (abscissa axis) for 115 evaluations in feet plantar skin of newborn live children. In the displayed scattering, the colors of the blue, green and red dots correspond to the reflectance values measured from the lights emitted by the blue, green and red LEDs respectively.

The graph depicted in FIG. 2 represents the relative reflectivity between LEDs of the same color with different distances relative to the photodiode for 115 live evaluations of the skin of live newborns. LEDs of the same color were used at different distances in order to obtain the ratio between the reflectances.

A decrease in relative reflectivity for newborns is observed for the blue color, and later for full-term infants an increase thereof. There are two distinct behaviors between said preterm or premature babies and those born at term. The results obtained by the prototype enable it to be used by at least three different methods of measuring gestational age, by means of the index of erythema and the reflectivity of the skin (epidermis and dermis). With two different ways of obtaining gestational age we can develop a process implemented through a computer program to obtain gestational age with greater accuracy by using artificial intelligence techniques. If we add the photobiological properties to the clinical information as factors of the model, this will be even closer to the values of the gestational age of the gold standard that corresponds to the model based on the obstetric ultrasound had up to the 13 weeks of pregnancy, as will be presented in example 2 of this patent document.

Example 2—Models for Predicting Gestational Age from Photobiological Properties of the Skin and Clinical Parameters of the Newborns Models for predicting gestational age at birth are based on photobiological properties of the skin such as reflectance or reflectivity by measuring the diffused or scattered portions of the light beam on the skin, as well as erythema index along with clinical parameters of the newborn such as the gender, the use of phototherapy, birth weight and incubator stay.

Using data from the study presented in Example 1 of this patent document together with gestational age values obtained with obstetric ultrasound had up to 13 weeks of pregnancy, three models were obtained for predicting gestational age at birth; 1) Model 1: determination of gestational age at birth from photobiological skin properties: red light scattering; 2) Model 2: determination of gestational age at birth from photobiological properties of the skin: erythema index red and blue light scattering; 3) Model 3: determination of gestational age at birth from photobiological skin properties; erythema index, red and blue color light scattering and clinical parameters of newborns. Models 1, 2 and 3 will be presented in topics I, II and III, respectively.

Figure 3:
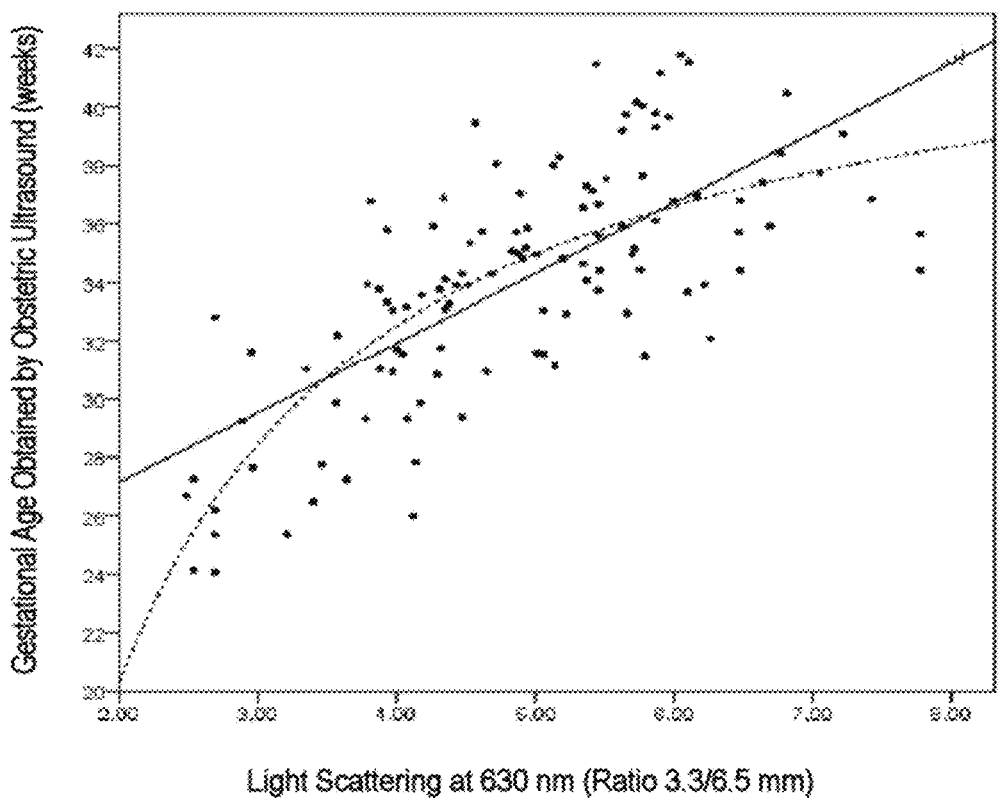
FIG. 3 shows a graph of red light scattering (625-635 nm) across the skin as a function of gestational age obtained by means of obstetric ultrasound had up to 13 weeks of pregnancy. There are represented in the ordinate axis the values of gestational age in weeks and in the abscissa axis the ratio between red light scattering values (625-635 nm) measured at distances of 2-4 and 4-7 mm with respect to the sensor. The dots represent the observed values, the continuous and dashed lines respectively represent the linear and inverse regressions obtained from the observed values.

I. Model 1: Determination of Gestational Age at Birth from Photobiological Skin Properties Red Light Scattering This model is described in a scatter plot representing the scattering of red light (630 nm) across the skin as a function of the gestational age obtained by means of obstetric ultrasound had up to 13 weeks of pregnancy, according to FIG. 3. On the ordinate axis, the values of gestational age in weeks are represented and on the abscissa axis the ratio of red light scattering values (630 nm) measured at distances of 3.3 and 6.5 mm in relation to the sensor is represented. The points represent the observed values, the solid and dashed lines represent, respectively, the linear and inverse regressions obtained from the observed values, which expressions are: 1) linear regression: GA=2.40X+22.35 and 2) inverse regression: GA=44.75−(48.93/X); their significance values (p) and coefficient of determination ($R^2$) are $p<0.01$ and 0.51, $p<0.01$ and 0.56, respectively, where X is the ratio of values of red light scattering (630 nm) measured at distances of 3.3 and 6.5 mm with respect to the sensor.

Figure 4:
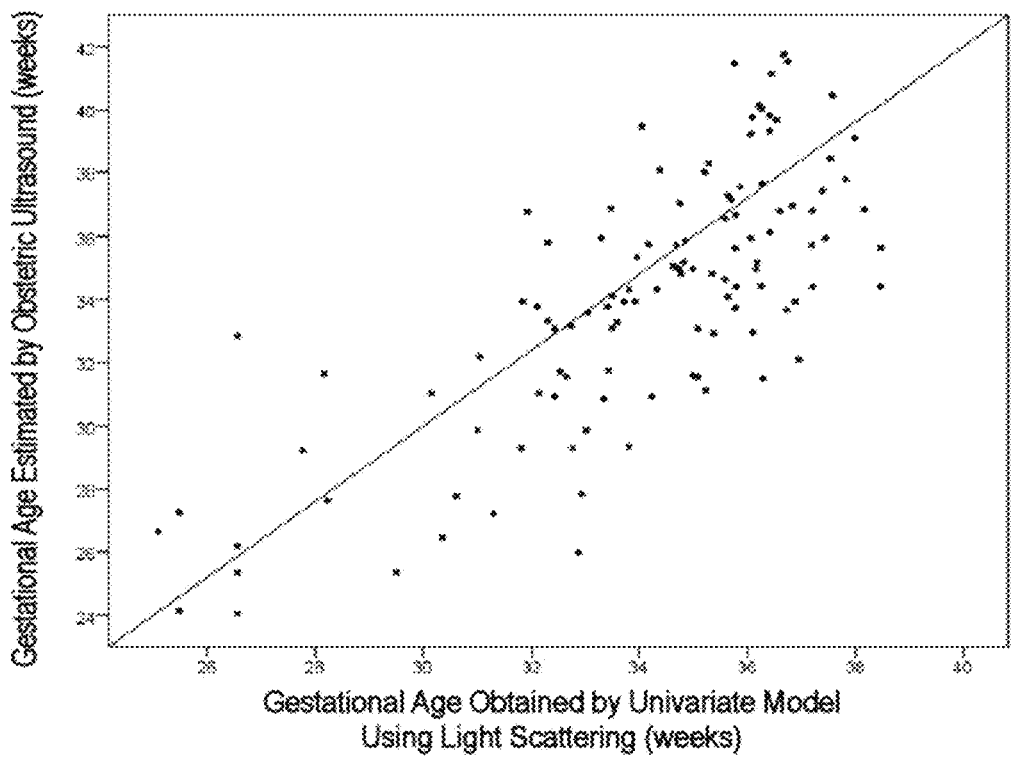
FIG. 4 shows a graph representing the scattering carried out from the values of gestational age (weeks) obtained by obstetric ultrasound had up to 13 weeks of pregnancy (ordinate axis) as a function of gestational age (weeks) obtained by measuring the red light scattering (625-635 nm) by the skin performed at distances of 2-4 and 4-7 mm with respect to the sensor (abscissa axis). The solid line represents the linear regression of the values of the scattering.

Upon comparing the proposed model with the known model based on obstetric ultrasound had up to 13 weeks of pregnancy, a graph is achieved representing the scattering from the values of gestational age (weeks) obtained by means of the obstetric ultrasound had up to 13 weeks of pregnancy (ordinate axis) according to the gestational age (weeks) obtained by measuring the red light scattering (630 nm) by the skin at distances of 3.3 and 6.5 mm with respect to the sensor (abscissa axis), as shown in FIG. 4. The solid line represents the linear regression (the values of significance (p) and correlation coefficient (R) are $p<0.001$ and 0.71). It is possible to perceive the good correspondence between the proposed model and the model based on obstetric ultrasound had up to 13 weeks of pregnancy forming part of the state of the art.

II. Model 2: Determination of Gestational Age at Birth from Photobiological Skin Properties: Red and Blue Light Scattering and Erythema Index This model describes the scattering of red and blue light (630 nm and 470 nm) across the skin as a function of the gestational age obtained by means of obstetric ultrasound had up to 13 weeks of pregnancy. The values of gestational age as a function of the ratio of red light scattering values (630 nm) measured at distances of 3.3 and 6.5 mm with respect to the sensor, scattering of the green light (535 nm) measured at the distance of 3.3 mm with respect to the sensor, blue light scattering (470 nm) measured at the distance of 3.3 mm with respect to the sensor and the erythema index according to expression (1) were adjusted according to a regression, which expression was described in the specification and is identified as expression (3); the values of significance (p) and coefficient of determination ($R^2$) are $p<0.01$ and 0.686.

Figure 5:
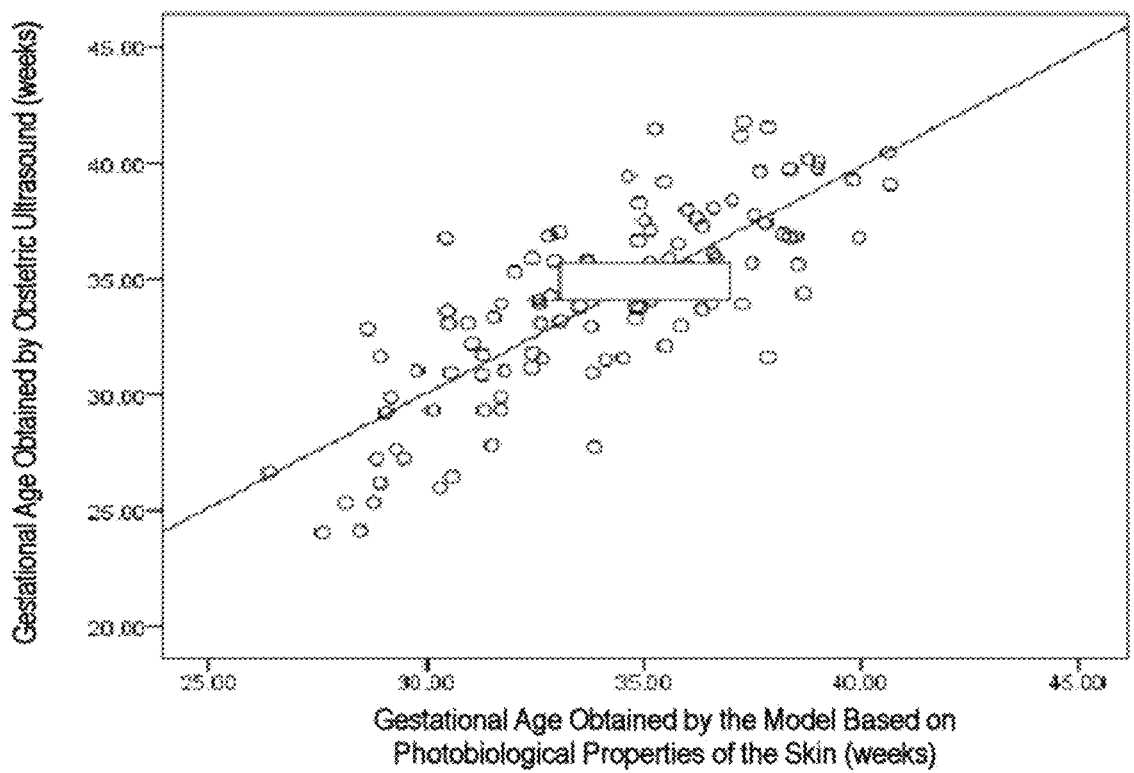
FIG. 5 shows a graph representing the scattering carried out from the values of gestational age (reeks) obtained by means of a multivariate model using only skin photobiological properties (relative reflectivity between red LEDs and the reflectivity of the blue LIED), represented in the abscissa axis, as a function of the values of the gestational age obtained by obstetric ultrasound had up to 13 weeks of pregnancy (ordinate axis). The solid line represents the linear regression of the values of the scattering.

Upon comparing the proposed model with the known model based on obstetric ultrasound had up to 13 weeks of pregnancy, a graph is achieved representing the scattering from the values of gestational age (weeks) obtained by means of the obstetric ultrasound had up to 13 weeks of pregnancy (ordinate axis) according to the gestational age (weeks) obtained by means of the proposed model, as shown in FIG. 5. The solid line represents the linear regression (values of significance (p) and correlation coefficient (R) are $p<0.001$ and 0.828). It is possible to perceive the good correspondence between the proposed model and the model based on obstetric ultrasound had up to 13 weeks of pregnancy forming part of the state of the art.

III. Model 3: Determination of Gestational Age at Birth from Photobiological Skin Properties: Erythema Index, Red and Blue Color Light Scattering, and Clinical Parameters of Newborns This model relates the erythema index, red and blue light scattering (630 nm and 470 nm) across the skin together with clinical parameters of newborns as a function of gestational age obtained by means of obstetric ultrasound had up to 13 weeks of pregnancy. The values of gestational age as a function of the ratio of red light scattering values (630 nm) measured at distances of 3.3 and 6.5 mm with respect to the sensor, scattering of the green light (535 nm) measured at the distance of 3.3 mm with respect to the sensor, blue light scattering (470 nm) measured at the distance of 3.3 mm with respect to the sensor and the erythema index according to expression (1) together with the clinical parameters such as the gender of the newborn (being attributed 0 or 1 if male or female, respectively), presence in the incubator at the time of measurement with the device (attributed 0 or 1 if absent or present, respectively), and use of phototherapy at the time of measurement with the device (0 or 1 if not in use or in use, respectively) and birth weight (in grams). These data were adjusted according to a regression whose expression was described in the specification and is identified as expression (4) the values of significance (p) and coefficient of determination ($R^2$) are $p<0.01$ and 0.829.

Figure 6:
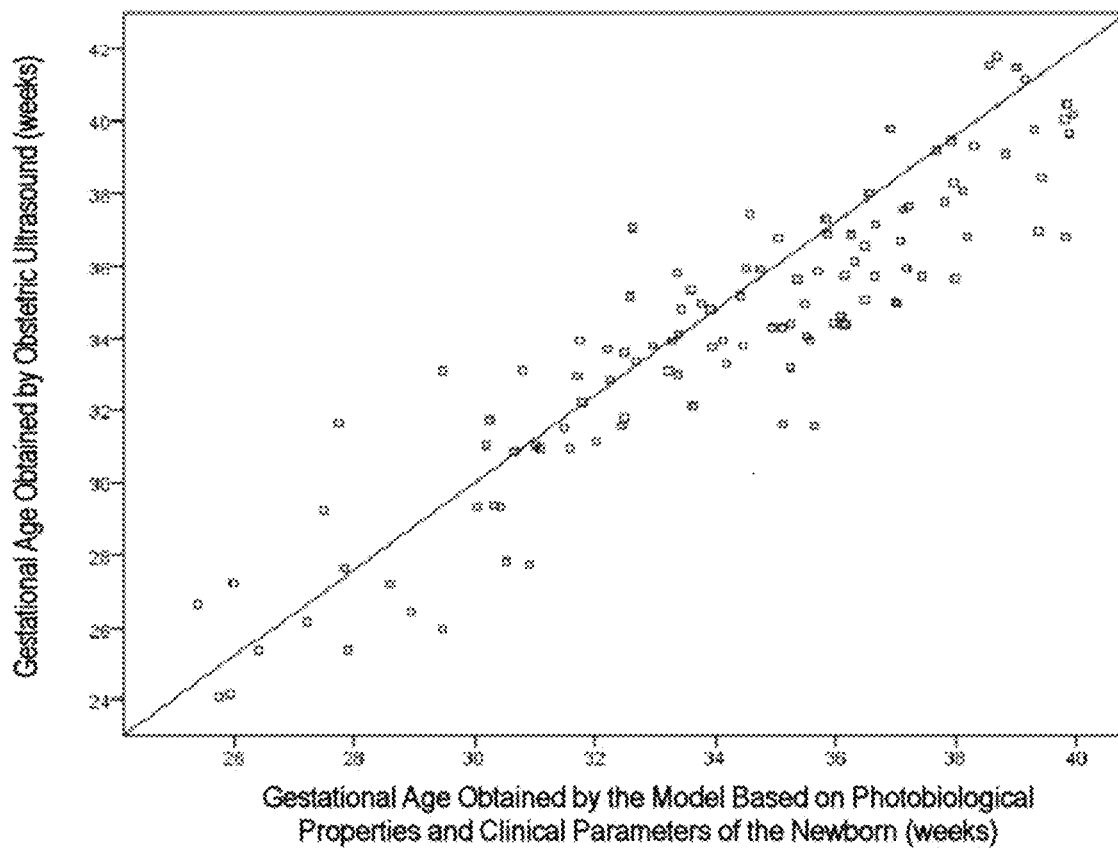
FIG. 6 shows a graph representing the scattering carried out from the values of gestational age (weeks) obtained by means of a multivariate model using skin photobiological properties (relative reflectivity between red LEDs and the reflectivity of the blue LED and erythema index), together with clinical parameters of the newborn (gender, use of phototherapy, birth weight and incubator stay), represented in the abscissa axis, as a function of gestational age values obtained by obstetric ultrasound had up to 13 weeks of pregnancy (ordinate axis). The solid line represents the linear regression of the values of the scattering.

In a comparison of the proposed model with the known model based on obstetric ultrasound had up to 13 weeks of pregnancy, a graph representing the achieved scattering from the values of gestational age (weeks) obtained by means of obstetric ultrasound had up to 13 weeks of pregnancy (ordinate axis) according to the gestational age (weeks) obtained by means of the proposed model, according to FIG. 6. The solid line represents the linear regression (the values of significance (p) and correlation coefficient (R) are $p<0.001$ and 0.91). It is possible to perceive the good correspondence between the proposed model and the model based on obstetric ultrasound had up to 13 weeks of pregnancy forming part of the state of the art.

The invention claimed is:

1. A device for determining gestational age of a newborn, said device comprising a holder and at least one computer, said holder configured to enclose at least one light emitter element and at least one sensor element,
   wherein the at least one light emitter element is configured to shine a light beam of 440-635 nm wavelength, and
   wherein the at least one sensor element is configured to capture part of a light signal emitted by the at least one light emitter element and reflected or diffused by the foot of the newborn, and
   wherein the at least one sensor element is configured to convert the light signal into a light intensity measurement, and
   wherein the at least one sensor element is positioned at a distance of 2-4 mm from the at least one light emitter element; and
the at least one computer configured to:
   receive the light intensity measurement, determine an erythema index based on the light intensity measurement, and
   determine gestational age by inputting the light intensity measurement, the erythema index, and one or more parameters selected from the group consisting of gender, a use of phototherapy, birth weight, and incubator status into a multivariate equation.

2. The device, according to claim 1, wherein the at least one light emitter element is configured to shine light at wavelengths within at least one range selected from the group consisting of 440-485, 625-635, and 530-540.

3. The device according to claim 2, wherein the at least one light emitter element is a light emitting diode (LED) and the at least one sensor element is a photodiode.

4. The device according to claim 2, wherein the at least one light emitter element further comprises a plurality of light emitter elements having the same wavelength,
   wherein said plurality of light emitter elements are spaced apart from the at least one sensor element at different distances, and
   wherein the spacing between said plurality of light emitter elements and the at least one sensor element is configured for cancellation of light signal interferences.

5. The device according to claim 1, wherein the at least one light emitter element is a light emitting diode (LED) and the at least one sensor element is a photodiode.

6. The device according to claim 5, wherein the at least one light emitter element further comprises a plurality of light emitter elements having the same wavelength,
   wherein said plurality of light emitter elements are spaced apart from the at least one sensor element at different distances, and
   wherein the spacing between said plurality of light emitter elements and the at least one sensor element is configured for cancellation of light signal interferences.

7. The device according to claim 1, wherein the at least one light emitter element further comprises a plurality of light emitter elements having the same wavelength,
   wherein said plurality of light emitter elements are spaced apart from the at least one sensor element at different distances, and
   wherein the spacing between said plurality of light emitter elements and the at least one sensor element is configured for cancellation of light signal interferences.

8. A method for determining a gestational age of a newborn comprising
a) sensing photobiological properties of the newborn with the device of claim 1 by
  i) shining, from the at least one light emitter element, the light beam having a wavelength within the range of 440-635 nm on the foot of the newborn,
  ii) obtaining at least one light intensity measurement reflected or diffused by the light beam,
  iii) determining the erythema index based on the at least one light intensity measurement, and
b) calculating the gestational age by inputting the at least one light intensity measurement, the erythema index, and one or more parameters selected from the group consisting of gender of the newborn, a use of phototherapy of the newborn, birth weight of the newborn, and incubator status of the newborn into a multivariate equation.

9. The method according to claim 8, wherein step b) further comprises selecting a value for said one or more parameters selected from the group of the gender, the use of phototherapy, the birth weight and the incubator status of the newborn, wherein the value for
the gender of the newborn is 1 for male or 0 for female;
the use of phototherapy is 1 for yes and 0 for no;
the use of the incubator is 1 for yes and 0 for no;
the birth weight of the newborn is the value in grams; and
determining the gestational age of the newborn by inputting at least one of said selected values in step b) within the multivariate equation.

10. The method according to claim 9, wherein step i) and step ii), further includes:
1) shining a light beam, from the at least one light emitting element, with 625-635 nm of wavelength on the foot of a newborn and
2) obtaining at least one light intensity measurement resulting from step 1) with the light beam using a sensor positioned at a distance of 2-4 mm from the at least one light emitting element;
3) shining, from the at least one light emitting element, a light beam with 625-635 nm of wavelength on the foot of the newborn and
4) obtaining at least one light intensity measurement resulting from step 3) with the light beam using a sensor positioned at a distance of 4-7 mm from the at least one light emitting element;
5) shining, from the at least one light emitting element, a light beam with 440-485 nm of wavelength on the foot of the newborn and
6) obtaining at least one light intensity measurement resulting from step 5) with the light beam using a sensor positioned at a distance of 2-4 mm from the at least one light emitting element;
7) shining, from the at least one light emitting element, a light beam with 530-540 nm of wavelength on the foot of the newborn and
8) obtaining at least one light intensity measurement resulting from step 7) with the light beam using a sensor positioned at a distance of 2-4 mm from the at least one light emitting element;
wherein step b) further includes:
A) calculating a ratio ($x_1$) between the at least one light intensity measurement from step 2) and step 4); wherein the at least one light intensity measurement at the distance of 4-7 mm from step 4) is divided by the at least one light intensity measurement at the distance of 2-4 mm in step 2);
B) calculating a logarithm for the base 10 ($x_3$) of the subtraction between the at least one light intensity measurement from step 2) and step 4);
C) selecting the value of the birth weight of the newborn in grams;
D) selecting the value for the gender of the newborn, wherein 1 is for male and 0 for female;
E) selecting the value for the use of the incubator, wherein 1 is for yes and 0 is for no;
F) selecting the value for the use of phototherapy; wherein 1 is for year and 0 is for no; and
G) calculating a gestational age (GA), in weeks, using the multivariate equation, wherein the multivariate equation is equation (4):

$$GA=12.143-20.995x_1+(3.544\times10^{-6})x_2+3.746x_3+0.002x_4-0.179x_5-0.855x_6-0.403x_7 \quad (4),$$

by replacing the value of the ratio ($x_1$) obtained in step A) with the variable ($x_1$) of equation (4), the value of the reflectance obtained in step 6) with the variable ($x_2$) of equation (4); the value of the logarithm obtained in step B) with the variable ($x_3$) of equation (4); the value of the newborn weight selected in step C) with the variable ($x_4$) of equation (4); the value of the newborn gender selected in step D) with the variable ($x_5$) of equation (4); the value for the use of the incubator selected in step E) with the variable ($x_6$) of equation (4); the value for the use of phototherapy obtained in step F) with the variable ($x_7$) of equation (4).

11. The method according to claim 8, wherein step i) and step ii), further includes:
1) shining, from the at least one light emitter element, a light beam with 625-635 nm of wavelength on the foot of the newborn and
2) obtaining at least one light intensity measurement from the at least one light emitter element using the at least one sensor positioned at a distance of 2-4 mm from the at least one light emitter element;
3) shining, from the at least one light emitter element, a light beam with 625-635 nm of wavelength on the foot of the newborn and
4) obtaining at least one light intensity measurement from the light beam using the at least one sensor positioned at a distance of 4-7 mm from the at least one light emitter element;
wherein step b) further includes:
A) calculating a ratio (x) between the at least one light intensity measurement in step 2) and the at least one light intensity measurement in step 4); and
B) calculating a gestational age (GA), in weeks, using the multivariate equation, wherein the multivariate equation is equation (2):

$$GA=44.75-(48.93/x)$$

by inputting the value of the ratio (x) obtained in step A) as the variable (x) of equation (2).

12. The method according to claim 8, wherein step i) and step ii), further includes:
1) shining the light beam, from the at least one light emitter element, with 625-635 nm of wavelength on the foot of a newborn and
2) obtaining at least one light intensity measurement resulting from step 1) with the at least one light beam using the at least one sensor positioned at a distance of 2-4 mm from the at least one light emitting element;

3) shining the light beam from the at least one light emitting element with 625-635 nm of wavelength on the foot of the newborn and
4) obtaining at least one light intensity measurement resulting from step 3) with the light beam using the at least one sensor positioned at a distance of 4-7 mm from the at least one light emitting element;
5) shining the light beam, from the at least one light emitting element, with 440-485 nm of wavelength on the foot of the newborn and
6) obtaining at least one light intensity measurement resulting from step 5) with the light beam using the at least one positioned at a distance of 2-4 mm from the at least one light emitting element;
7) shining a light beam, from the at least one light emitting element, with 530-540 nm of wavelength on the foot of the newborn and
8) obtaining at least one light intensity measurement resulting from step 7) with the light beam using a sensor positioned at a distance of 2-4 mm from the at least one light emitting element;

wherein step b) further includes:
A) calculating a ratio ($x_1$) between the at least one light intensity measurement from step 2) and step 4); wherein the at least one light intensity measurement at the distance of 4-7 mm from step 4) is divided by the at least one light intensity measurement at the distance of 2-4 mm in step 2);
B) calculating a logarithm for the base 10 ($x_3$) of the subtraction between the at least one light intensity measurement from step 2) and step 4); and
C) calculating a gestational age (GA), in weeks, using the multivariate equation, wherein the multivariate equation is equation (3):

$$GA=1.995x_1+(1.156\times10^{-5})x_2+9.357x_3-31.767, \quad (3)$$

by replacing the value of the ratio ($x_1$) obtained in step A) with the variable ($x_1$) of equation (3), the value of the reflectance obtained in step 6) with the variable ($x_2$) of equation (3); the value of the logarithm obtained in step B) with the variable ($x_3$) of equation (3).

13. The method according to claim 8, wherein step i) and step ii), further includes:
1) shining, from the at least one light emitting element, the light beam having a wavelength of 625-635 nm on the foot of the newborn and
2) obtaining at least one light intensity measurement resulting from step 1) with the light beam using a sensor positioned at a distance of 2-4 mm from the at least one light emitting element;
3) shining, from the at least one light emitting element, a light beam with 625-635 nm of wavelength on the foot of the newborn and
4) obtaining at least one light intensity measurement resulting from step 3) with the light beam using a sensor positioned at a distance of 4-7 mm from the at least one light emitting element;
5) shining a light beam, from the at least one light emitting element, with 440-485 nm of wavelength on the foot of the newborn and
6) obtaining at least one light intensity measurement resulting from step 5) with the light beam using a sensor positioned at a distance of 2-4 mm from the at least one light emitting element;
7) shining a light beam, from the at least one light emitting element, with 530-540 nm of wavelength on the foot of the newborn and
8) obtaining at least one light intensity measurement resulting from step 7) with the light beam using a sensor positioned at a distance of 2-4 mm from the at least one light emitting element;

wherein step b) further includes:
A) calculating a ratio ($x_1$) between the at least one light intensity measurement from step 2) and step 4); wherein the at least one light intensity measurement at the distance of 4-7 mm from step 4) is divided by the at least one light intensity measurement at the distance of 2-4 mm in step 2);
B) calculating a logarithm for the base 10 ($x_3$) of the subtraction between the at least one light intensity measurement from step 2) and step 4);
C) selecting the value of the birth weight of the newborn in grams;
D) selecting the value for the gender of the newborn, wherein 1 is for male and 0 for female;
E) selecting the value for the use of the incubator, wherein 1 is for yes and 0 is for no;
F) selecting the value for the use of phototherapy; wherein 1 is for year and 0 is for no; and
G) calculating a gestational age (GA), in weeks, using the multivariate equation, wherein the multivariate equation is equation (4):

$$GA=12.143-20.995x_1+(3.544\times10^{-6})x_2+3.746x_3+0.002x_4-0.179x_5-0.855x_6-0.403x_7 \quad (4),$$

by replacing the value of the ratio ($x_1$) obtained in step A) with the variable ($x_1$) of equation (4), the value of the reflectance obtained in step 6) with the variable ($x_2$) of equation (4); the value of the logarithm obtained in step B) with the variable ($x_3$) of equation (4); the value of the newborn weight selected in step C) with the variable ($x_4$) of equation (4); the value of the newborn gender selected in step D) with the variable ($x_5$) of equation (4); the value for the use of the incubator selected in step E) with the variable ($x_6$) of equation (4); the value for the use of phototherapy obtained in step F) with the variable ($x_7$) of equation (4).

\* \* \* \* \*